(12) United States Patent
Mantilla et al.

(10) Patent No.: US 8,777,885 B2
(45) Date of Patent: Jul. 15, 2014

(54) WRIST SUPPORT DEVICE

(76) Inventors: Alberto Mantilla, Rego Park, NY (US);
Anthony John Baxter, Upper Montclair, NJ (US); Paul Michael Elhardt, Charlotte, NC (US); Thomas Chilton Hill, Charlotte, NC (US)

(*) Notice: Subject to any disclaimer, the term of this patent is extended or adjusted under 35 U.S.C. 154(b) by 39 days.

(21) Appl. No.: 13/029,211

(22) Filed: Feb. 17, 2011

(65) Prior Publication Data

US 2012/0116277 A1    May 10, 2012

Related U.S. Application Data

(60) Provisional application No. 61/306,173, filed on Feb. 19, 2010.

(51) Int. Cl.
*A61F 5/00*    (2006.01)

(52) U.S. Cl.
USPC .................. 602/21; 602/16; 602/62; 128/878

(58) Field of Classification Search
USPC ............ 602/16, 21–22, 62–64; 128/877–880; 2/16–17, 21
See application file for complete search history.

(56) References Cited

U.S. PATENT DOCUMENTS

| | | | |
|---|---|---|---|
| 5,921,945 A * | 7/1999 | Gray | 602/5 |
| 6,539,550 B1 * | 4/2003 | Flores | 2/16 |
| 8,137,296 B2 * | 3/2012 | Chiang et al. | 602/21 |

FOREIGN PATENT DOCUMENTS

WO    WO 2009115661 A1 *    9/2009

OTHER PUBLICATIONS

Machine Translation of WO2009115661, Patent Translate, pp. 1-9.*

* cited by examiner

*Primary Examiner* — Patricia Bianco
*Assistant Examiner* — Kari Petrik
(74) *Attorney, Agent, or Firm* — Jeffrey Sonnabend; SonnabendLaw (57) ABSTRACT

An apparatus for supporting a patient's hand, wrist, and at least a portion of the forearm in order to expose the radial artery to receive an arterial line. The apparatus including a substantially flexible, unitary body adapted to underlie the posterior of the patient's hand, wrist and forearm. The unitary body including a forward portion having an upturned cutout portion for receiving finger portions of a patient's hand. The forward portion configured for mating engagement with the posterior surface of the hand. The unitary body further including a rear portion sloping downward from the forward portion and having an upturned cutout portion for receiving a forearm portion of a patient.

2 Claims, 11 Drawing Sheets

WRIST SUPPORT DEVICE

REFERENCE TO RELATED APPLICATION

This patent claims priority of U.S. Provisional Patent Application Ser. No. 61/306,173, filed on Feb. 19, 2010 and incorporated herein by reference.

FIELD OF THE INVENTION

This invention relates to arm supporting devices generally and more specifically to a device for supporting and positioning a patient's hand, wrist, and a portion of the forearm for administering arterial or intravenous therapy.

BACKGROUND OF THE INVENTION

Individuals undergoing medical care in a hospital environment commonly require arterial therapy (e.g., invasive monitoring of blood gases) or the infusion of intravenous fluids, particularly during and after surgery. It is important in such therapy that the patient's wrist be properly oriented in an angled position to easily receive and start the arterial or intravenous line. Thus, there exists a need for an economic, convenient and effective apparatus for supporting a patient's wrist and forearm for such therapy.

Traditionally, arterial and intravenous lines have been administered by supporting the patient's arm on an improvised armboard formed by a flat piece of rigid cardboard or wood and securing the patient's arm thereto with strips of adhesive tape. Towels or other padding materials have been positioned beneath the patient's wrist to properly angle the wrist to receive and start the arterial or intravenous line. The padding materials are removed once the line has been started. Such prior techniques are tedious and utilize the time of valuable hospital personnel who would otherwise be free to perform other duties. In addition, the materials used in constructing such armboards are not always readily available and are relatively costly.

The traditional armboards, moreover, often do not properly position the patient's wrist to receive the line and are typically uncomfortable for the patient. Because prior armboards have not normally been shaped to accommodate the contours of the patient's arm, a relatively hard surface is presented which does not conform to the shape of the patient's arm. Adhesive tape is thus required to stabilize the arm, such tape tends to abrade hair and skin in the contact areas and frequently causing adverse skin reactions.

It is also not uncommon with the traditional technique for a patient to accidentally disconnect the arterial or intravenous line by flexing his wrist, or for a nurse or other medical professional to require substantial time to start the arterial or intravenous line. Aside from the costly nature of such start-up time and required restarts, the time for starting and restarting the line may be detrimental to the patient's welfare.

In an attempt to obviate the above disadvantages associated with the traditional armboards, wrist supporting apparatus were provided typically in the configuration of a preformed unitary support. The preformed unitary support apparatus typically used foam block pieces and/or VELCRO brand straps in attempt to immobilize the patient's wrist and thus prevent wrist flexing to position the patient's wrist at the proper angle for accurate and efficient handling of the arterial or venous puncture. However, it has been found that VELCRO brand straps stretch and lose their ability to maintain wrist extension over time, requiring staff time to reposition or replace them while increasing both patient and facility risk due to dampened waveforms, infection, false blood-pressure reading, etc. Additionally, it has been found foam block pieces shrink, changes shape and move due to patient activity, sliding action of rigid supports, sweat/moisture, etc. Also, foam has been found to be uncomfortable when performing daily activities and requires time to position and re-position to ensure proper function.

SUMMARY OF THE INVENTION

In one aspect, a device for supporting and positioning a patient's hand, wrist, and a portion of the forearm for administering arterial or intravenous therapy is described in which an aspect of the invention includes a substantially flexible, unitary body adapted to underlie the posterior of the patient's hand, wrist and forearm. The unitary body may include a forward portion having an upturned cutout portion for receiving finger portions of a patient's hand. The forward portion may be configured for mating engagement with the posterior surface of the hand. The unitary body further may include a rear portion sloping downward from the forward portion and having an upturned cutout portion for receiving a forearm portion of a patient.

In further, optional aspects, the foregoing apparatus includes an adjustment mechanism integrally formed in the unitary body at a position intermediate the forward and rear portions of the unitary body. The adjustment mechanism is configured and operable to manipulate the forward portion at a desired angle relative to the rear portion.

The invention is advantageous to assist high-risk surgical patients based on their respiratory, cardiac disease, and overall health, and all surgical patients that require arterial blood gases or blood draws during surgery. In particular, the apparatus improves staff efficiency and patient safety in at least the following settings: ICU, cardiac telemetry, step-down units, cardiac-ICU, military and pediatric care facilities. The apparatus is also advantageous during the following procedures: heart, cardiovascular, endovascular with AAA stent placements, and general surgery; transplants (liver, kidney, heart, lung), thoracotomies (lung lobectomies, wedge resections); and generally, any surgeries requiring at least 4 hours to complete.

It is to be appreciated the invention as described in accordance with the illustrated embodiments dramatically reduces the need for arterial line reinsertion and adjustments, increasing healthcare efficiency and safety, reducing administrative costs and, most importantly, improving patient outcomes.

BRIEF DESCRIPTION OF THE DRAWINGS

The objects and features of the invention can be understood with reference to the following detailed description of an illustrative embodiment of the present invention taken together in conjunction with the accompanying drawings in which.

WRITTEN DESCRIPTION OF CERTAIN EMBODIMENTS OF THE INVENTION

The present invention is now described more fully with reference to the accompanying drawings, in which an illustrated embodiment of the present invention is shown. The present invention is not limited in any way to the illustrated embodiment as the illustrated embodiment described below is merely exemplary of the invention, which can be embodied in various forms, as appreciated by one skilled in the art. Therefore, it is to be understood that any structural and functional details disclosed herein are not to be interpreted as limiting, but merely as a basis for the claims and as a representative for teaching one skilled in the art to variously employ the present invention. Furthermore, the terms and phrases used herein are not intended to be limiting but rather to provide an understandable description of the invention.

Figure 1:
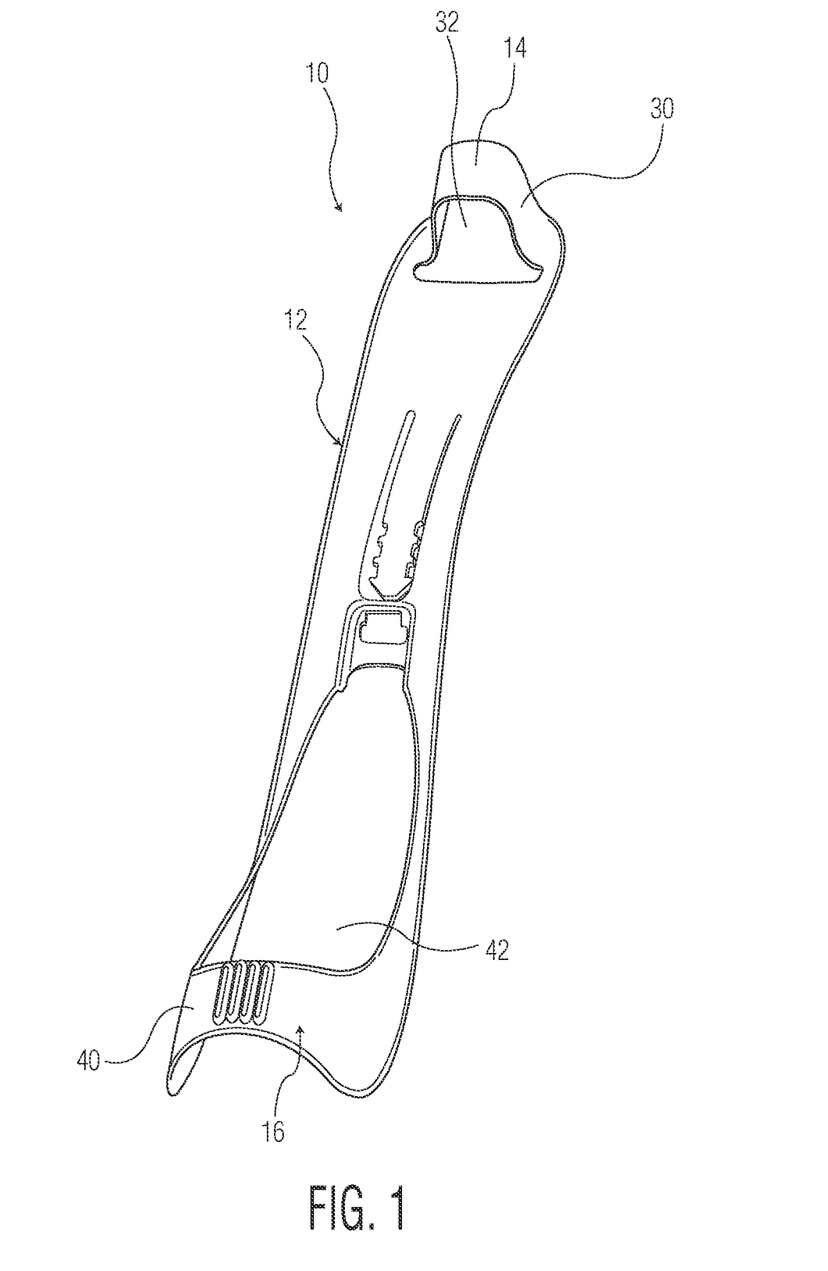
FIG. 1 is a perspective view of the arterial wrist support in accordance with an illustrated embodiment of the invention.

Referring now to the drawings, wherein like reference numerals designate like or corresponding parts throughout the views, FIG. 1 shows a perspective representation of the arterial wrist support device of the present invention. The device 10 includes a substantially flexible molded unitary body 12 adapted to matingly engage the top portion of the patient's hand, wrist and at least a bottom portion of the patient's forearm to support the patient's arm in a substantially relaxed position for arterial care.

Figure 2:
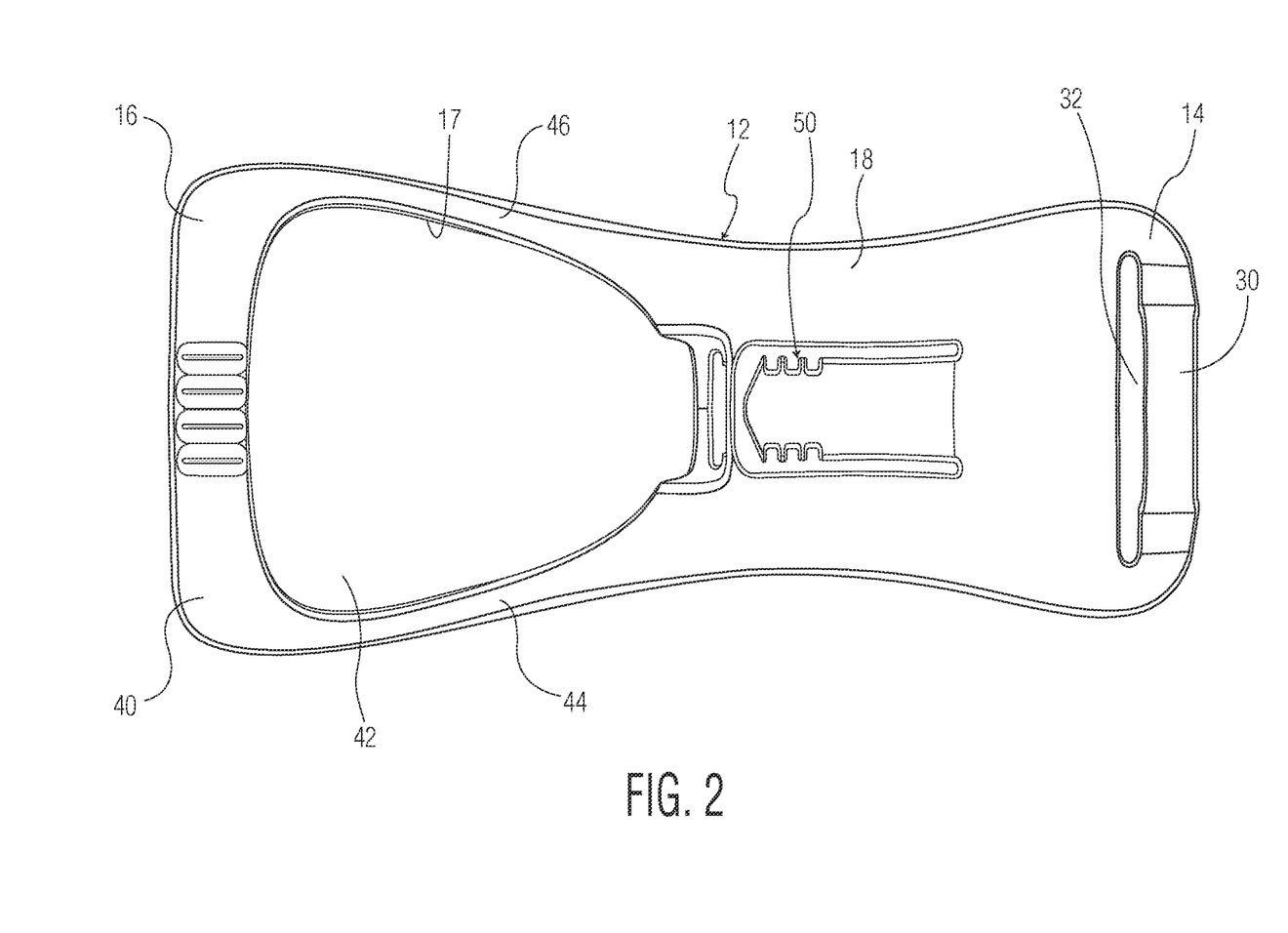
FIG. 2 is a top view of the arterial wrist support of FIG. 1.
Figure 3:
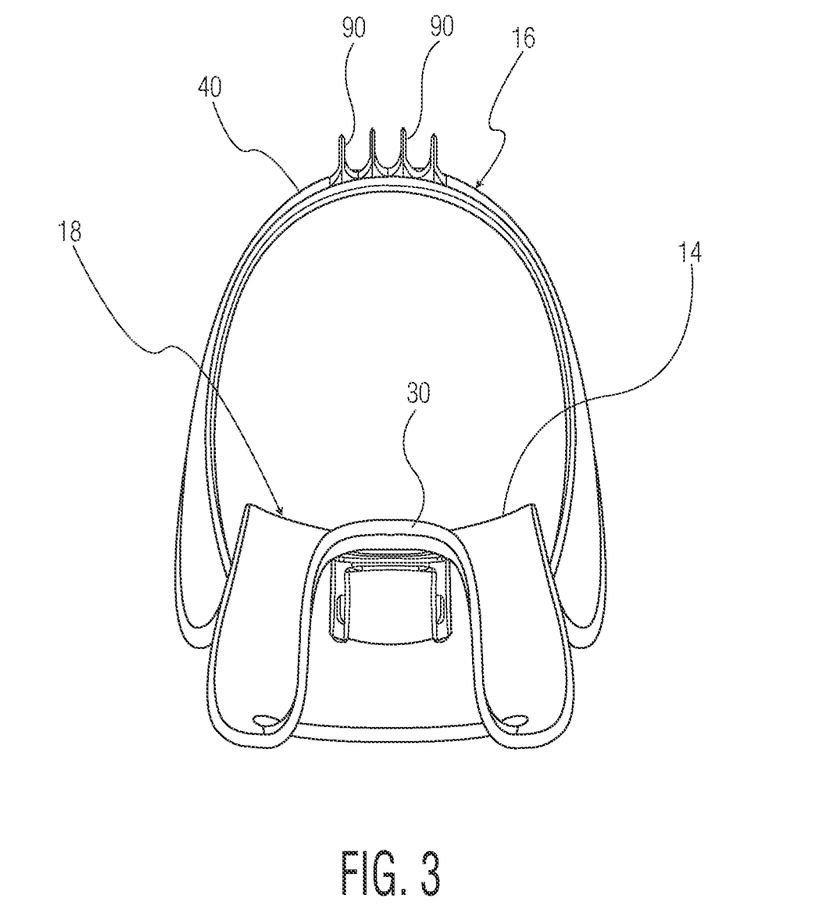
FIG. 3 is a front view of the arterial wrist support of FIG. 1.
Figure 4:
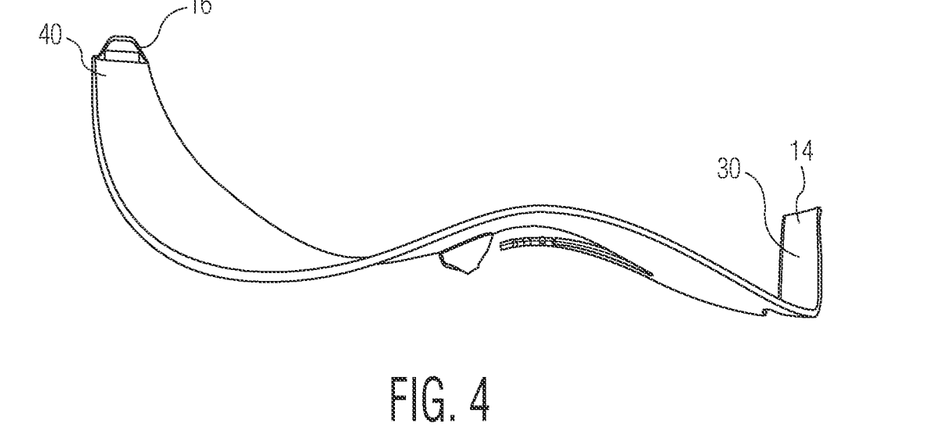
FIG. 4 is a side view of the arterial wrist support of FIG. 1.
Figure 5:
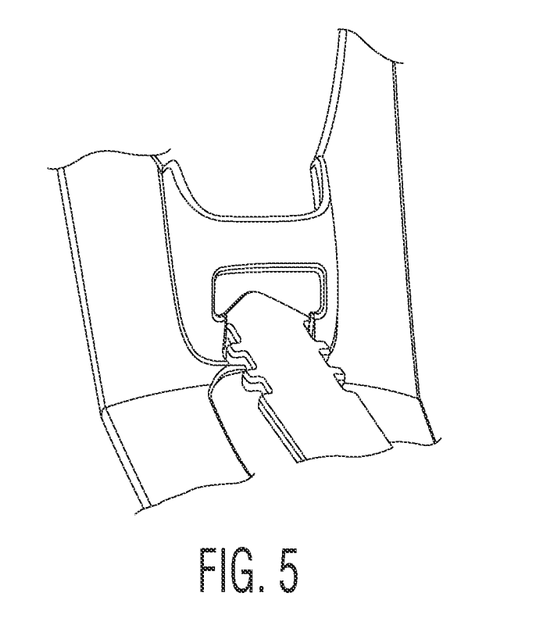
FIG. 5 is a detailed view of the adjustment mechanism of the arterial wrist support of FIG. 1.
Figure 6:
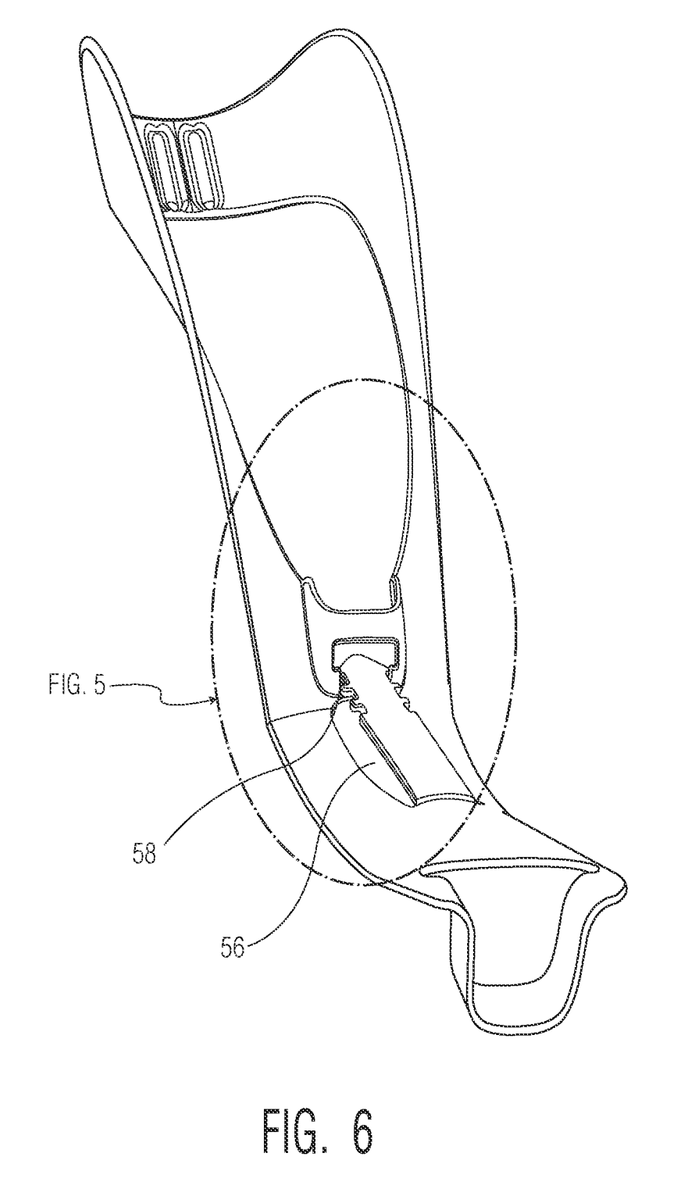
FIG. 6 is a perspective view of the arterial wrist support illustrating use of the adjustment mechanism of the arterial wrist support of FIG. 1.
Figure 7:
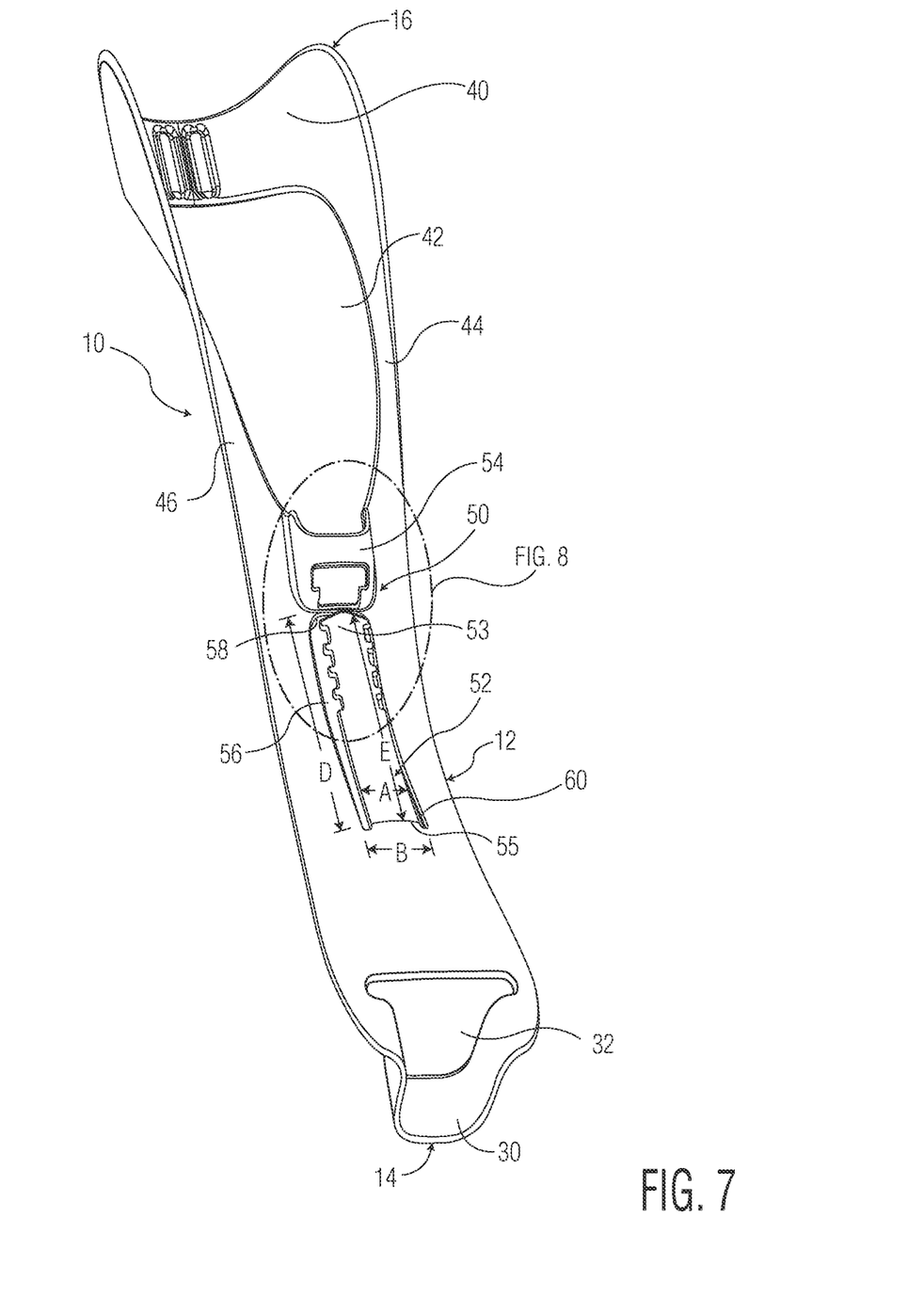
FIG. 7 is a perspective view of the arterial wrist support of FIG. 1.

Body 12 includes a forward portion 14 for receiving the top of the patient's hand and a rear portion 16 integrally connected thereto for receiving the patient's wrist and forearm. Forward portion 14 is spoon-shaped, as shown in FIG. 2, is substantially concave at the upper surface as shown in FIG. 3, and slopes downwardly from rear portion 16, as shown in FIG. 4. As discussed further below, rear portion 16 is formed with a forearm cutout portion 42 configured to receive a portion of the patient's forearm. Rear portion 16 is substantially concave and contoured to fit and conform with a patient's forearm. A transversely arcuate channel 18 extends and is defined along the mid-section of the molded body 12 to the forward portion 14 to define a cradle contoured portion to receive atop the patient's wrist and hand. As also to be further discussed below, device 10 includes an adjustment mechanism 50 operable to position the forward portion 14 at an adjustable angle relative to the rear portion 16 to orient a patients wrist at multiple wrist extension angles for arterial therapy.

Body 12 may be formed of any suitable rigid material which may be formed in the desired shape. In the preferred embodiment, body 12 is preferably formed of a recyclable high-nsity polyethylene (HDPE) material, injection molded to the contoured configuration described herein.

Figure 12:
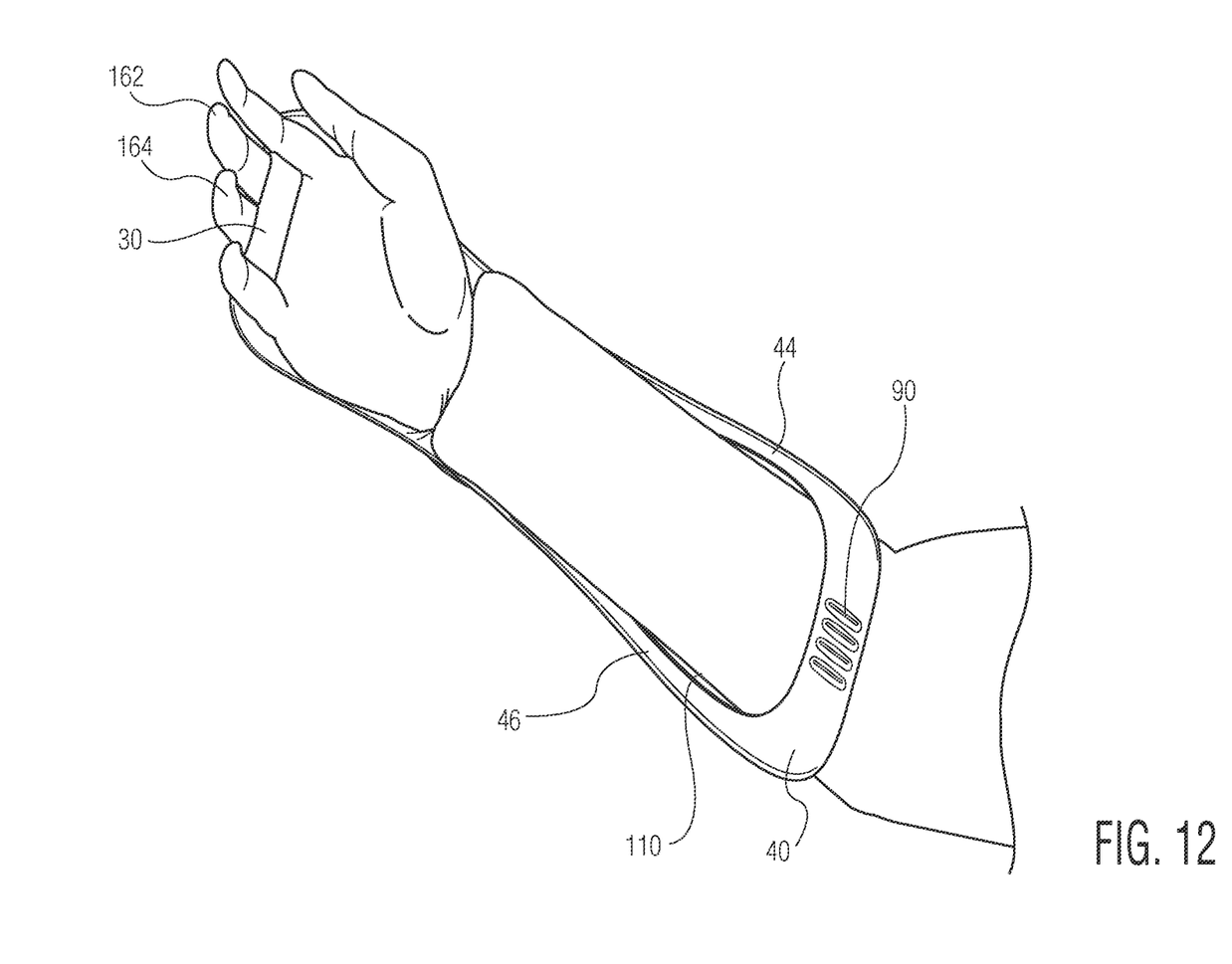
FIG. 12 is a perspective view of the arterial wrist support of FIG. 1 fitted to a patient.

With continued reference to FIGS. 1-4, the forward portion 14 of device 10 includes an integrally formed upturned portion 30 defining a finger cutout portion 32 configured to preferably receive the patients middle finger 102 and ring finger 104 (FIG. 12). The integrally formed upturned portion 30 is operable to stabilize a patients hand and wrist portion against the contoured surface of the forward portion 14 of the device 10 during arterial therapy.

Similarly, the rear portion 16 of device 10 includes an integrally formed forearm upturned forearm portion 40 defining an elongated forearm cutout portion 42 configured to receive the patients forearm 110 (FIG. 12). The elongated forearm cutout portion 42 is defined by sloping side portions 44, 46 and a rear contoured portion defined by the upturned portion 40 and a forward contoured portion formed by a portion of the adjustment locking mechanism 50, as described below. The integrally formed forearm upturned portion 40 is operable to stabilize the device 10 against a patients forearm portion 110 while the forearm upturned portion 40 is resting against the bottom portion of a patient's forearm 110. The sloping side portions 44, 46 are supported against the side portions of a patient's forearm 110 extending from a bottom portion to a top portion of the patient's forearm while the front contoured portion of the elongated cutout 42 is resting against a top portion of the patient's forearm in close proximity to the top portion of the patient's wrist.

Referring now to FIGS. 5-8, the adjustment locking mechanism 50 is integrally formed with body portion 12 and includes an engagement member 52 adapted to detachably receive within a locking receiving member 54. The engagement member 52 extends within an elongated cutout portion 56. The elongate cutout portion 56 is defined along the longitudinal axis defined by elongate body portion 12 and is formed in the mid-section of body 12 having a first end 58 formed adjacent the locking receiving member 54 and a second opposing end 60 in spaced relationship from the finger cutout portion 32. The engagement member 52 has a first end 53 spaced from the first end 58 of cutout portion 56 and a second end 55 integrally formed with and extending from the second end 60 of the elongate cutout portion 56. The engagement member 52 has a width "A" which is less than the width "B" of the cutout portion 56 and length "C" that is less than the length "D" of the elongate cutout portion 56 whereby engagement member 52 is resiliently flexible within the cutout portion 56.

Figure 8:
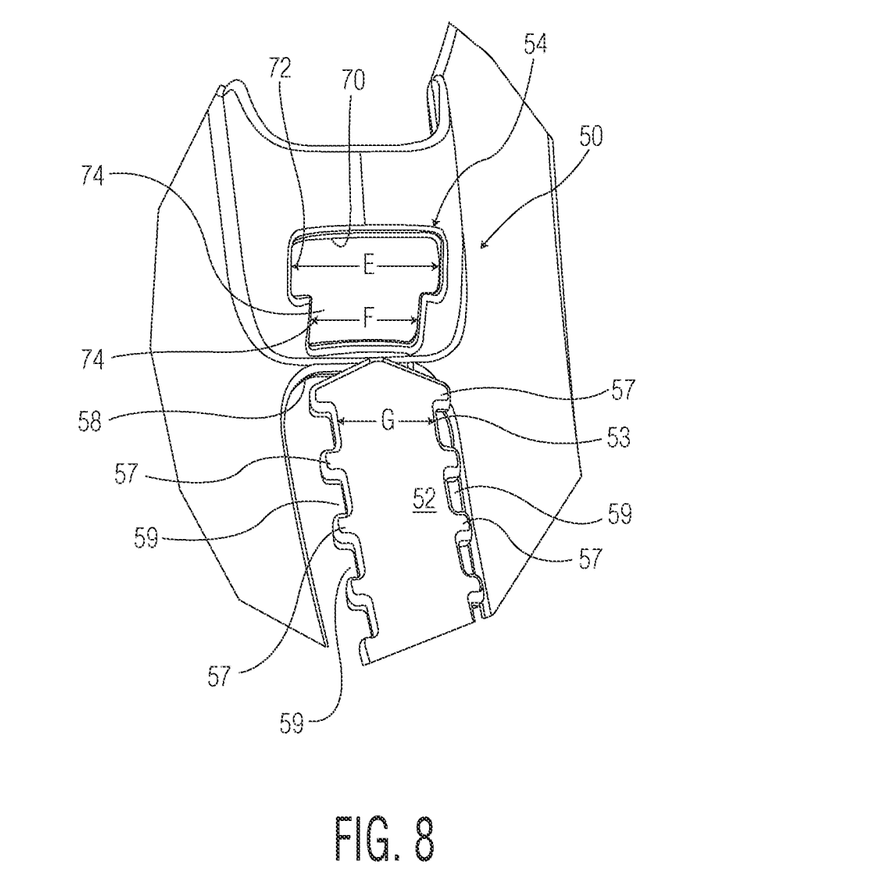
FIG. 8 is a detailed view of the adjustment mechanism of the arterial wrist support of FIG. 1.

As best shown in FIG. 8, the first end portion 53 of engagement member 52 includes a plurality of detent members 57 formed along the side portions of engagement member 52 defining a locking channel 59 between adjacent detent members 57. As discussed below, these detent members 57 and defined locking channels 59 are configured and operable to enable the engagement member 52 to adjustably, and detachably, engage with the locking portion 54 of the adjustment locking mechanism 50 so as to orient a patients wrist at multiple wrist extension angles, via the movement of the forward portion 14.

With continuing primary reference to FIG. 8, the locking portion 54 of the adjustment mechanism 50 is preferably defined by a T-shaped cutout portion 70 wherein a top portion 72 has a width "E" greater than the width "A" of the engagement member 52 and bottom portion 74 defined by a width "F" less than the width "A" of the engagement member 52 but greater than the width "G" defined on the engagement member 52 between locking channels 59 disposed on a common axis perpendicular to the longitudinal axis defined by the engagement member 52. Thus, the first end 53 of engagement member 52 is configured and operable to slideably receive in the top portion 72 of the T-shaped cutout portion 70 and may be positioned downward into the bottom portion 74 between locking channels 59 defining an adjustment setting, wherein the engagement member 52 is detachably engaged therewithin until it is moved by a user upward towards the top portion 72 of the T-shaped cutout portion 70.

Figure 9:
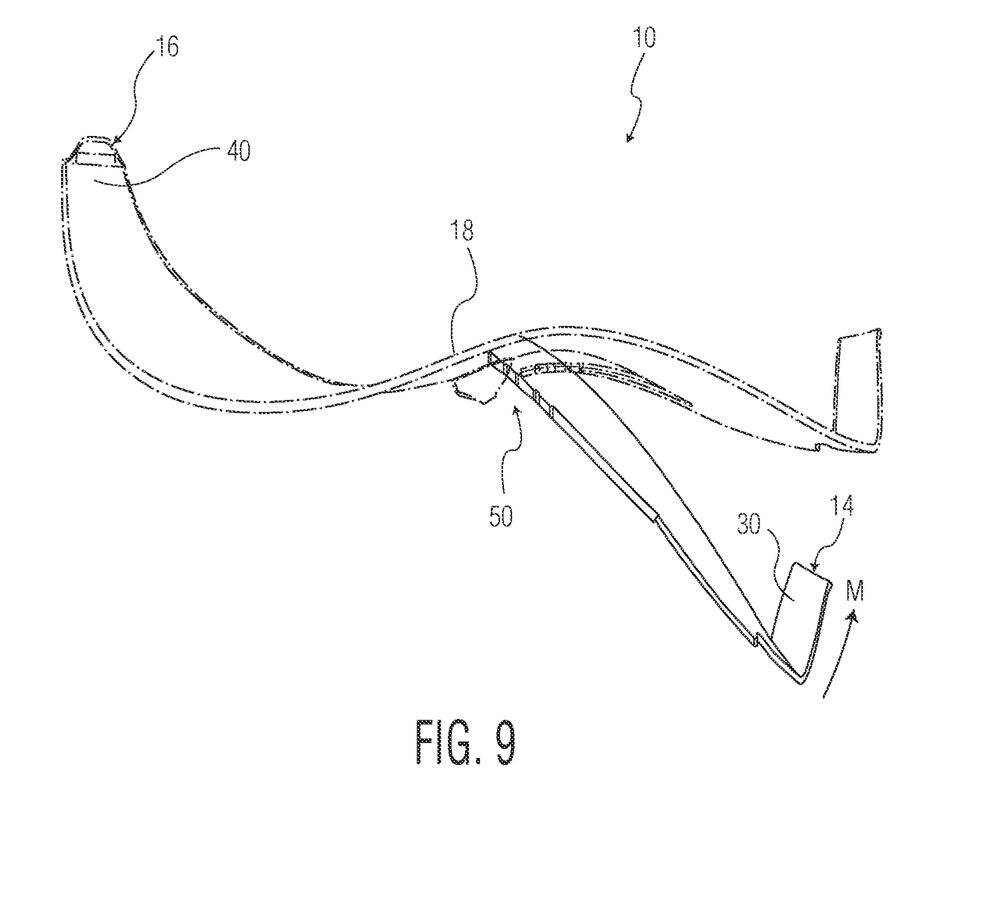
FIG. 9 is a side view of the arterial wrist support of FIG. 1 illustrating adjustability of a forward portion.
Figure 10:
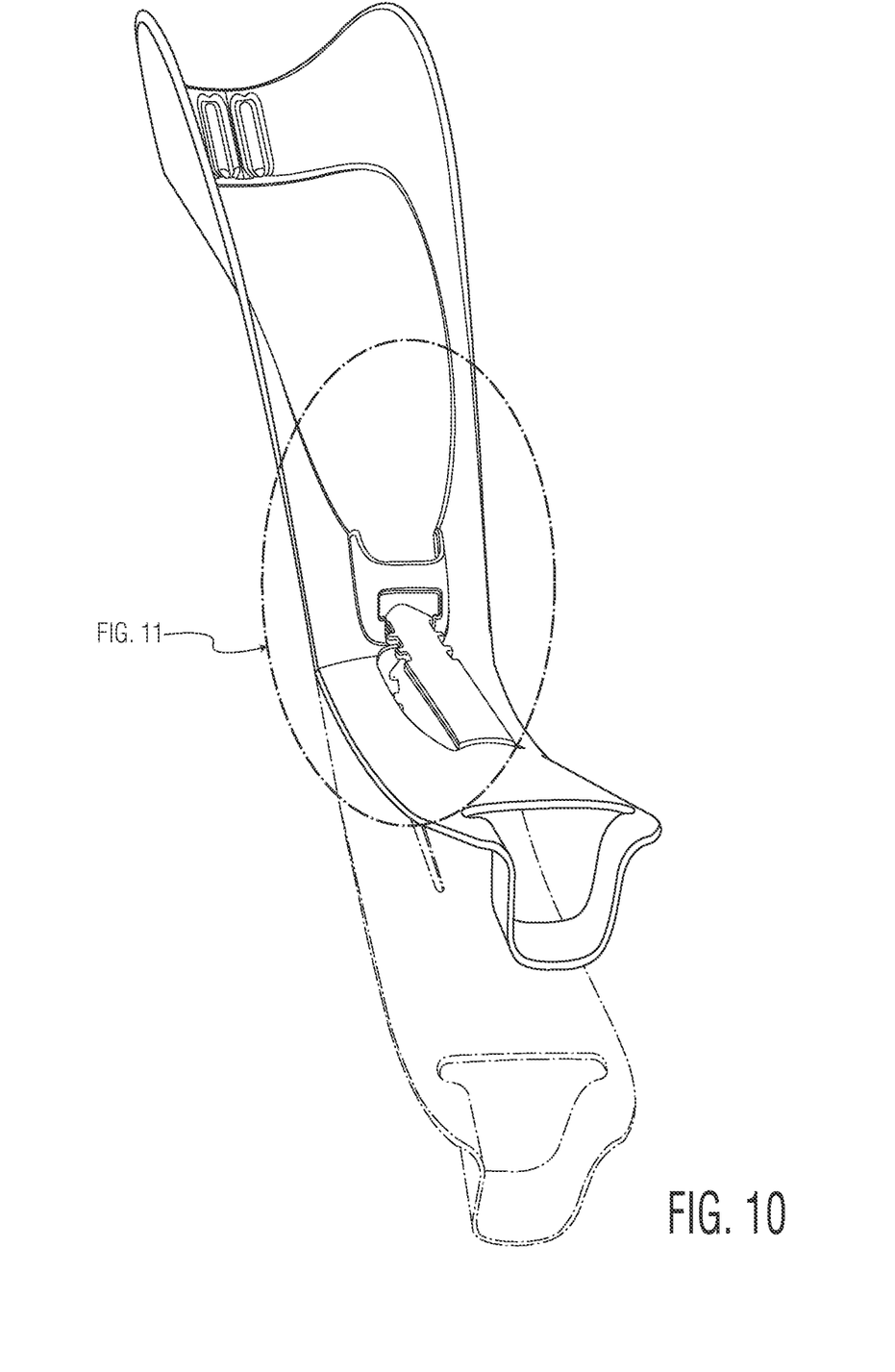
FIG. 10 is a perspective view of the arterial wrist support of FIG. 1 illustrating adjustability of a forward portion.
Figure 11:
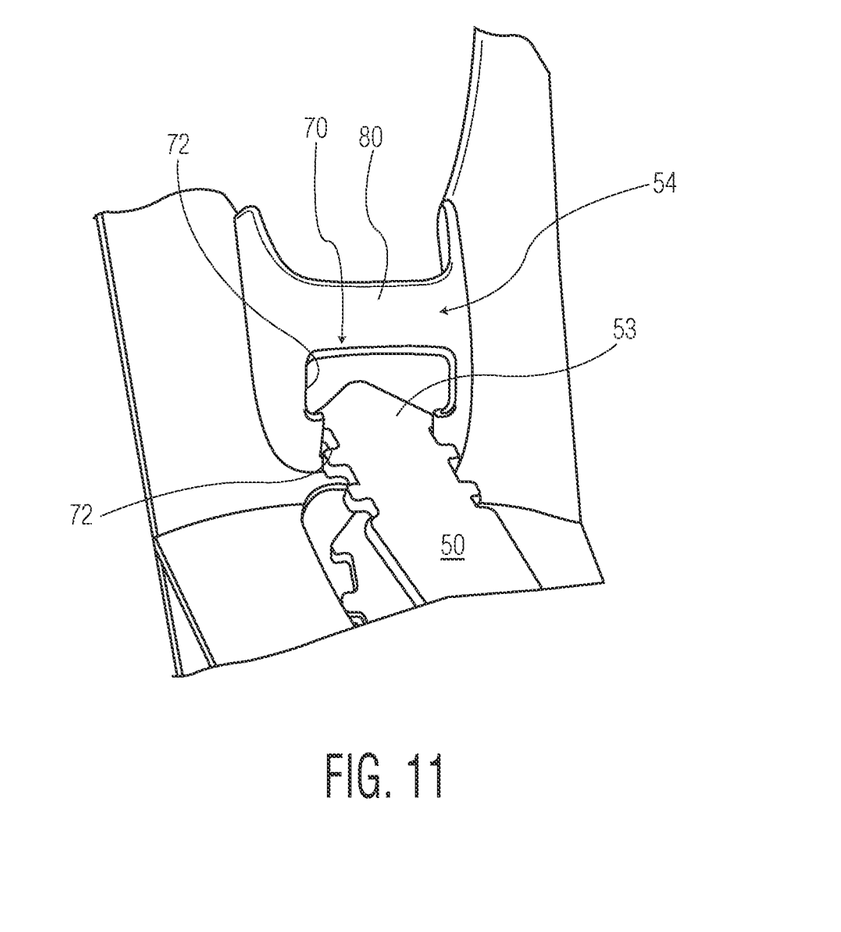
FIG. 11 is a detailed perspective view of the adjustment mechanism of the arterial wrist support of FIG. 10.

As best shown in FIGS. 9-11, it is to be appreciated that when the first end 53 of engagement member 52 is detachably engaged in the bottom portion 74 of T-shaped cutout portion 70, the first portion 14 of device 10 is caused to resiliently bend downwards relative to it's second portion 16 causing the first portion 14 of device 10 to bias upwards (FIG. 9). With reference now to FIGS. 10 and 11, this causes the detent members 57 to be biased against the outer walls defining the bottom locking cutout portion 74 thus locking the first portion 14 of device 10 at its angled orientation relative to the second portion of device 10, the adjustability of which will be further described below.

As best shown in FIG. 8, the locking portion 54 of adjustment mechanism 50 is defined on a spherical projection 80 integrally formed on the body 12 of device 10. Particularly, the T-shaped cutout portion 70 is formed on a curved surface of spherical projection facing towards the first end 53 of engagement member 50 to facilitate ease of insertion therewithin.

FIG. 12 illustrates the initial positioning of the patient's wrist in device 10 to start an arterial line. As shown, the patient simply manipulates their hand and forearm portion through the forearm upturned portion 40 such that the patients ring 104 and middle fingers 102 are received within the integrally formed upturned finger portion 30 with the patient's wrist resting against the contoured surface of the forward portion 14 of the device 10. The integrally formed forearm upturned portion 40 rests against a bottom portion of the patients forearm with the sloping side portions 44, 46 supported against the side portions of a patient's forearm 110.

The patients wrist may be caused to turn upwards via the adjustment mechanism 50 whereby the engagement member 52 is inserted into the locking receiving portion 54 and engaged therewithin via engagement of desired locking channels 56 within the bottom locking portion 74 of the T-shaped cutout portion 70 such the patient's wrist is immobilized at a desired angle so an arterial line can be held in the desired position.

Device 10 also includes structure to support arterial lines via a plurality of upstanding arterial line support walls 90 extending from the upturned forearm portion 40. The arterial line support walls 90 are preferably spaced apart from one another a distance sufficient to receive an arterial line and retaining it therewithin preferably via a friction fit.

In summary, an arterial wrist support device has been disclosed to support a patient's arm in a comfortable and relaxed position for arterial therapy. The device is contoured to fit the shape of the patient's arm, and is anatomically shaped and adjustably to manipulate the patient's wrist at a desired and proper angle to expose the radial artery for accurate, efficient handling of the arterial puncture. The device is unitarily formed and is adjustable to orient a patients wrist at multiple wrist extension angles significantly eliminating dampened waveforms caused by the a-line catheter being pushed up against the arterial wall when the wrist is in a neutral or flexed position. The device is configured to be fitted to the patient by the patient without requiring an additional person due to the obviation of VELCRO straps (or adhesive tape) typically used on prior art devices. The device 10 is ergonomically designed for comfort while providing a range of motions such that a patient can perform normal activities without constraint, e.g., writing, using the telephone, puling themselves out of bed, eating, reading, etc. Device 10 may also include pressure point padding to ensure long-term comfort and stable positioning even when the patient is sweating, restless, or skin is irritated.

Although the preferred embodiment has been described in detail, it should be understood that various changes, substitution and alterations can be made therein without departing from the spirit and scope of the invention as defined by the appended claims.

What is claimed is:

1. A wrist support device, comprising:
   a unitary body adapted to underlie a patient's hand, wrist, and forearm, said body including:
   a forward portion having an upturned cutout portion for receiving finger portions of the patient's hand, said forward portion configured for mating engagement with the posterior surface of the patient's hand; and
   a rear portion sloping downward from said forward portion and having an upturned cutout portion for receiving a portion of the patient's forearm;
   said cutout portion of said forward portion being located at one end of said body and said cutout portion of said rear portion being located at the other end of said body and said cutout portions extending in the same direction from said body;
   an adjustment mechanism integrally formed in said unitary body at a position intermediate said forward portion and said rear portion of said unitary body and positioned between said forward portion and said rear portion, said adjustment mechanism configured and operable to manipulate said forward portion at a desired angle relative to said rear portion, said adjustment mechanism comprising a locking device, said locking device including a tongue portion and a slot portion adapted for receiving said tongue portion.

2. The device as recited in claim 1, wherein said tongue portion includes teeth.

* * * * *